United States Patent
Goyal et al.

(10) Patent No.: US 12,042,321 B2
(45) Date of Patent: *Jul. 23, 2024

(54) SYSTEM AND METHODS FOR ASSESSING PRESENCE OF LARGE VESSEL OCCLUSION TO AID IN TRANSFER DECISION-MAKING FOR ENDOVASCULAR TREATMENT IN PATIENTS WITH ACUTE ISCHEMIC STROKE

(71) Applicant: MG Stroke Analytics Inc., Calgary (CA)

(72) Inventors: Mayank Goyal, Calgary (CA); Bijoy K. Menon, Calgary (CA)

(73) Assignee: MG Stroke Analytics Inc., Calgary (CA)

( * ) Notice: Subject to any disclaimer, the term of this patent is extended or adjusted under 35 U.S.C. 154(b) by 60 days.

This patent is subject to a terminal disclaimer.

(21) Appl. No.: 17/814,435

(22) Filed: Jul. 22, 2022

(65) Prior Publication Data
US 2022/0354446 A1   Nov. 10, 2022

Related U.S. Application Data

(63) Continuation of application No. 16/295,149, filed on Mar. 7, 2019, now Pat. No. 11,413,001.
(Continued)

(51) Int. Cl.
*A61B 6/00* (2024.01)
*A61B 6/03* (2006.01)
(Continued)

(52) U.S. Cl.
CPC ............ *A61B 6/5217* (2013.01); *A61B 6/032* (2013.01); *A61B 6/501* (2013.01); *A61B 6/504* (2013.01);
(Continued)

(58) Field of Classification Search
CPC ....... A61B 6/5217; A61B 6/032; A61B 6/504; A61B 6/507; A61B 6/5241; A61B 6/501;
(Continued)

(56) References Cited

U.S. PATENT DOCUMENTS 9,324,143 B2   4/2016   Goyal
2003/0018276 A1*  1/2003   Mansy ................... A61B 7/003
600/529

(Continued)

FOREIGN PATENT DOCUMENTS

WO   2014036638 A1   3/2014

OTHER PUBLICATIONS

Agarwal et al. 2015 Frontiers in Neurology 6 article 70 7pages (Year: 2015).*
(Continued)

*Primary Examiner* — Keith M Raymond
*Assistant Examiner* — Patrick M Mehl
(74) *Attorney, Agent, or Firm* — Whitmyer IP Group LLC

(57) ABSTRACT

The invention relates to systems and methods to assist physicians in decision making for stroke patients. In particular the systems and methods can be used to assist physicians to decide on whether a patient with an acute ischemic stroke has a large vessel occlusion (LVO) and should be transferred from a community hospital to a larger hospital to undergo an endovascular thrombectomy procedure.

13 Claims, 8 Drawing Sheets

Related U.S. Application Data

(60) Provisional application No. 62/639,914, filed on Mar. 7, 2018.

(51) Int. Cl.

| | | |
|---|---|---|
| *A61B 6/50* | (2024.01) | |
| *G06T 7/00* | (2017.01) | |
| *G06T 7/62* | (2017.01) | |
| *G16H 30/40* | (2018.01) | |

(52) U.S. Cl.
CPC ............ *A61B 6/507* (2013.01); *A61B 6/5241* (2013.01); *G06T 7/0016* (2013.01); *G06T 7/62* (2017.01); *G16H 30/40* (2018.01); *G06T 2207/10072* (2013.01); *G06T 2207/30016* (2013.01); *G06T 2207/30104* (2013.01)

(58) Field of Classification Search
CPC ....... A61B 6/481; A61B 6/486; G06T 7/0016; G06T 7/62; G06T 2207/30104; G06T 2207/10072; G06T 2207/30016; G06T 2200/04; G06T 2207/10081; G16H 30/40; G16H 50/20; G16H 30/20
See application file for complete search history.

(56) References Cited

U.S. PATENT DOCUMENTS

| | | | |
|---|---|---|---|
| 2016/0157800 A1* | 6/2016 | Goyal | A61B 6/486 |
| | | | 600/431 |
| 2016/0206816 A1 | 7/2016 | Pile-Spellman et al. | |
| 2019/0274652 A1 | 9/2019 | Goyal et al. | |

OTHER PUBLICATIONS

Kim et al. 2016 Eur. Radiol. 26:2974-2981 (Year: 2016).*
Naidich et al. 2003 Neuroradiology 45:536-540 (Year: 2003).*
Grunwald et al. 2007 in "Emergency Radiology: Imaging and Intervention" Marincek and Dondelinger Edts., Springer, 2007, Chapter 3.1 p. 293-311; Pub.Date 2007 (Year: 2007).*
Takahashi et al. 2015 J. Stroke Cerebrovascular Dis. 24:635-641 (Year: 2015).*
Takeuchi et al 2003 Neurol. Med. Chir. 43:153-162 (Year: 2003).*
Syste de Jong 2015 MS thesis Technical Medicine University of Twente 91 pages (Year: 2015).*
Takeuchi, Ryo, et al; "Fully Automated Quantification of Regional Cerebral Blood Flow With Thee-dimensional Stereotaxic Region of Interest Template: Validation Using Magnetic Resonance Imaging—Technical Note"; Journal of Neurologia medico-chirurgica, vol. 43, Issue 3; Apr. 1, 2003; 10 Pages.
Grunwald, I., et al.; "Emergency Radiology: Imaging and Intervention, Chapter 3.1"; Editors: Marincek and Dondelinger; Published by: Springer, Jan. 1, 2007, 20 Pages.
Agarwal, Smriti, et al.; "Is CT-Based Perfusion and Collateral Imaging Sensitive to Time Since Stroke Onset?"; Frontiers in Neurology, vol. 6, Article 70; Apr. 9, 2015; 7 Pages.
De Jong, Syste; "Quantifying Cerebral Blood Flow Of Both The Micro-And Macrovascular System Using Perfusion Computed Tomography"; Master Thesis, Technical Medicine, University of Twente; Radboud UMC, Nijmegen, Netherlands; Aug. 19, 2015; 91 Pages.
Kim, Eung Yeop; "Comparison of Imaging Selection Criteria for Intra-Arterial Thrombectomy in Acute Ischemic Stroke with Advanced CT"; European Society of Radiology Journals, vol. 26; Published by: Springer; Dec. 8, 2015; 8 Pages.
Menon, Bijoy K. et al.; "Multiphase CT Angiography: A New Tool for the Imaging Triage of Patients with Acute Ischemic Stroke"; Radiological Society of North America (RSNA), Radiology Article, vol. 275, No. 2; Jan. 29, 2015; 11 Pages.
Takahashi, Satoshi, et al.; "Comparison of Cerebral Blood Flow Data Obtained by Computed Tomography (CT) Perfusion with that Obtained by Xenon CT Using 320-Row CT"; Journal of Stroke and Cerebrovascular Diseases, vol. 24, No. 3; National Stroke Association; Mar. 2015; 7 Pages.
Neukirchen, Christoph, et al.; "An iterative method for tomographic x-ray perfusion estimation in a decomposition model-based approach"; Medical Physics, The International Journal of Medical Physics Research and Practice, vol. 37, Issue 2, Dec. 2010; First published: Nov. 8, 2010; 17 Pages.

* cited by examiner

Representative flow rates of contrast agent through an arterial region of the brain having affected and normal tissue

| | |
|---|---|
| A | Middle Cerebral Artery: Superior Division |
| B | Middle Cerebral Artery: Inferior Division |
| C | Middle Cerebral Artery: Lentinculostriate |
| D | Posterior Cerebral Artery |
| E | Anterior Cerebral Artery |
| F | Anterior Choroidal | mCTA delay map (left) of a 38 y/o female with TICI 0 and corresponding follow-up MR-DWI (right)

SYSTEM AND METHODS FOR ASSESSING PRESENCE OF LARGE VESSEL OCCLUSION TO AID IN TRANSFER DECISION-MAKING FOR ENDOVASCULAR TREATMENT IN PATIENTS WITH ACUTE ISCHEMIC STROKE

FIELD OF THE INVENTION

The invention relates to systems and methods to assist physicians in decision making for stroke patients. In particular the systems and methods can be used to assist physicians to decide on whether a patient with an acute ischemic stroke has a large vessel occlusion (LVO) and should be transferred from a community hospital to a larger hospital to undergo an endovascular thrombectomy procedure.

BACKGROUND OF THE INVENTION

When it is suspected that a person may have suffered a stroke, various processes are initiated to effect diagnosis and treatment. Generally, the initial steps include the initial recognition by the patient or family of various symptoms being exhibited by the patient and then effecting transportation of the patient to a care facility. Transportation is usually by ambulance or car.

Upon arrival at the care facility, typically an emergency department, depending on the abilities of the care facility, different diagnostic protocols will be initiated. Care facilities will have widely different capabilities ranging from small rural hospital facilities, to primary stroke care (PSC) facilities to larger comprehensive stroke care (CSC) facilities. Generally, if the primary physician initially suspects that a patient has had a stroke by noting symptoms such as sudden numbness or weakness in the face, arm, or leg, especially on one side of the body, sudden confusion, trouble speaking, or difficulty understanding speech, trouble seeing in one or both eyes, trouble walking, dizziness, loss of balance, or lack of coordination and/or a severe headache with no known cause, the physician will undertake a number of steps to effect a diagnosis. Initially, the physician will conduct a primary assessment to determine whether the patient has suffered a hemorrhagic or an ischemic stroke.

If the care facility is a primary stroke center (also referred to as a "not endovascular capable center") which are generally those centers having computed tomography (CT) equipment but not the capabilities of endovascular intervention, the physician would initially complete a computed tomography (CT) scan of the patient's brain to rule out a hemorrhagic stroke (i.e. a bleed) prior to proceeding with additional CT scans to determine if the stroke is an ischemic stroke. This initial high-level diagnosis is important in considering treatment options, including whether or not to administer clot-busting drugs but also, if the stroke appears serious enough, whether or not the patient should be transported to a comprehensive stroke center (also referred to as an "endovascular capable center"), namely a facility having the ability to conduct endovascular treatment options.

This latter step, namely the process by which a decision is made to transport or not transport a patient to a CSC will involve a wide range of factors including the time and distance from the PSC to the CSC, the availability of transportation to the CSC and also the severity of the stroke. Importantly, the decision requires a pragmatic balance between these factors. For example, for a given patient, if the CSC is too far away under current weather conditions, and/or ambulance/air transportation may not be immediately available, the time delay may be too much to obtain a beneficial outcome even if the patient makes it to the CSC.

Moreover, it is often current practice that upon delivery of a patient to an emergency department, the ambulance departs to either attend to other calls or leave to their standby position. As such, if the patient they transported to the PSC, is subsequently diagnosed with a stroke and requires transportation to a CSC, valuable time is wasted (typically up to 45 minutes) obtaining a new ambulance. While some of these factors can be mitigated by initiating protocols where an ambulance waits for a diagnostic study to be completed, this type of protocol only partially addresses the problem. In addition, these factors must be balanced against the best knowledge regarding the severity of the stroke and, it is this consideration that is often the most difficult for a PSC to make.

Importantly, while a PSC will be capable of CT scans, conducting the most appropriate scan (eg. CT angiogram or CT perfusion study) and interpreting that scan may not be possible in that the PSC will not be trained to plan for and conduct a CT scan to enable effective diagnosis of a large vessel occlusion (LVO).

As such, the quantitative assessment of the severity of a stroke requires the input of the CSC physicians. Currently, for example, most PSCs may not be able to conduct a CT perfusion study. Even when conducted the study must then be interpreted by a CSC physician via wide area network systems with diagnoses and decisions being made this way. However, this requires coordination between personnel at separate hospitals which can be a problem in itself as well as being subject to various technical inefficiencies and problems. These include difficulties resulting from the relatively long processing times for CT perfusion studies due to large data files and inaccuracies that may arise from patient movement. Also, depending on the billing models and systems, CSC physicians may not get paid for these reviews. Further still, a CT perfusion study is time-sensitive and the results may no longer be valid by the time the patient arrives at the CSC.

At the highest level, based on the American Heart Association (AHA) guidelines, patients with acute ischemic stroke who have ASPECTS (Alberta Stroke Program Early CT Score)>5 and have a large vessel occlusion (LVO) are eligible for endovascular thrombectomy (EVT).

Thus, there is a need at the PSC to determine as soon as possible after the patient arrives these two factors (i.e. ASPECTS and presence or not of LVO) usually based on a CT and CT angiogram. However, at most PSCs there is lack of trained personnel who can immediately assess and provide an interpretation on the imaging.

Also as noted earlier, the ideal workflow is if the paramedic staff that brought the patient in (and are familiar with the patient) are immediately able to take the patient to the CSC if the transfer was needed.

Thus ideally, if there was immediate interpretation, then there is the least amount of time being wasted to effect treatment especially given the clear correlation between time and outcome (time is brain).

Currently, there are now commercially available products available that can do automated ASPECTS reading e.g. Brainomix (Oxford, England).

However, problems with these approaches are that the studies and processes are limited in the quality of information for a broader range of cases and conditions. In other words, while effective for certain patients, they do not provide good information for a broader range of patients including older patients and those who may have old infarcts. Also, as different centers are conducting the scans, factors such as the age of the scanner, the amount of radiation and consistent imaging protocols may have an affect. This limits the accuracy of these softwares.

In addition, there is a need for rapid and/or early detection of LVO that is critical to the process of decision making.

SUMMARY OF THE INVENTION

In accordance with the invention, there is provided a method of assessing relative flows of contrast agent through a volume of brain tissue from a series of computed tomography angiogram (CTA) images to assist in diagnosing a large vessel occlusion (LVO), the method comprising the steps of: a) measuring contrast agent density across a plurality of CTA images obtained at different levels and displaying contrast agent density based on a color scale for different densities; b) over-layering boundaries of known vascular regions of each level and quantifying areas of affected tissue in the known vascular regions for each level; and c) calculating an area of affected tissue in a known region and based on a calculated area and threshold density values diagnose or not an LVO relevant to a particular region.

In another embodiment, the method further comprises the step of interpolating density values between the CTA images at different levels and calculating volumes of affected tissue in step c.

In one embodiment, a plurality of CT images are obtained using a multi-phase CTA (mCTA) protocol and the images of each phase are analyzed to calculate an area or volume of affected tissue by an analysis of all phases.

In another embodiment, each phase of CT images includes a time value and time differences between each phase and density values are used to calculate any one of or a combination of a rate of rise/fall in density, time of peak opacification and mean transit time (MTT).

In another embodiment, the rate and volume of contrast injection is known and correlated to density measurements.

In yet another embodiment, the multi-phase protocol includes 3 phases and phase 1 is timed to correspond to peak arterial flow of contrast through the contralateral side, phase 2 is timed to correspond to peak venous flow of contrast through the contralateral side and phase 3 is timed to correspond to flow of contrast from the ipsilateral side.

In one embodiment, the method further comprises the step of color coding each voxel of an image according to blood flow as calculated from any one of or a combination of time to peak, mean transit time and time to clear.

In one embodiment, the method is conducted from a single series of computed tomography angiogram (CTA) images.

In one embodiment, the method further comprises the step of calculating the phase of the single phase CTA images as early arterial, late arterial or venous based on a measurement of relative density of known arterial and venous structures during CTA imaging.

In one embodiment, variations in boundaries between vascular regions between patients are analyzed from a pool of past data and correlated to a current patient to improve determination of a patient's vascular regions and threshold values for diagnosing LVO.

In one embodiment, if the phase of the series of CTA images is not calculated and density measurements between the ipsilateral and contralateral sides are within a middle range, the system displays a warning to the physician that a mis-diagnosis is possible.

In another embodiment, the method is conducted from images of a CT perfusion (CTP) study and where CTP data may be used to calculate mean transit time and/or total volume of contiguous affected volume in 3D space.

In one embodiment of multi-phase CTA, the phase in which contrast density is maximal in the ipsilesional vs. contralesional hemisphere is measured and the difference between maximal density in the ipsilateral vs. contralateral side calculated as a phase delay value.

In one embodiment of multi-phase CTA, regions within the brain where contrast density does not change over phases is delineated and is marked as delayed washout.

In yet another embodiment, density values, phase delay, delayed washout, time value and time differences between each phase are used to calculate severity of ischemia beyond an arterial occlusion or beyond an identified LVO.

BRIEF DESCRIPTION OF THE FIGURES

The invention is described with reference to the accompanying figures in which.

DETAILED DESCRIPTION OF THE INVENTION

With reference to the figures, systems and methods for assisting PSC and CSC decision-making regarding stroke patients are described. More specifically, the systems and methods described assist a physician in deciding on the severity of a stroke and ultimately whether a stroke patient should be transferred from a PSC to a CSC where endovascular therapy is available, or whether a stroke patient should be kept at the first hospital. The system assists in making decisions including confirming the ASPECTS reading (that could be based on a local physician's interpretation or automated software) and/or presence/absence of an LVO.

Figure 1:
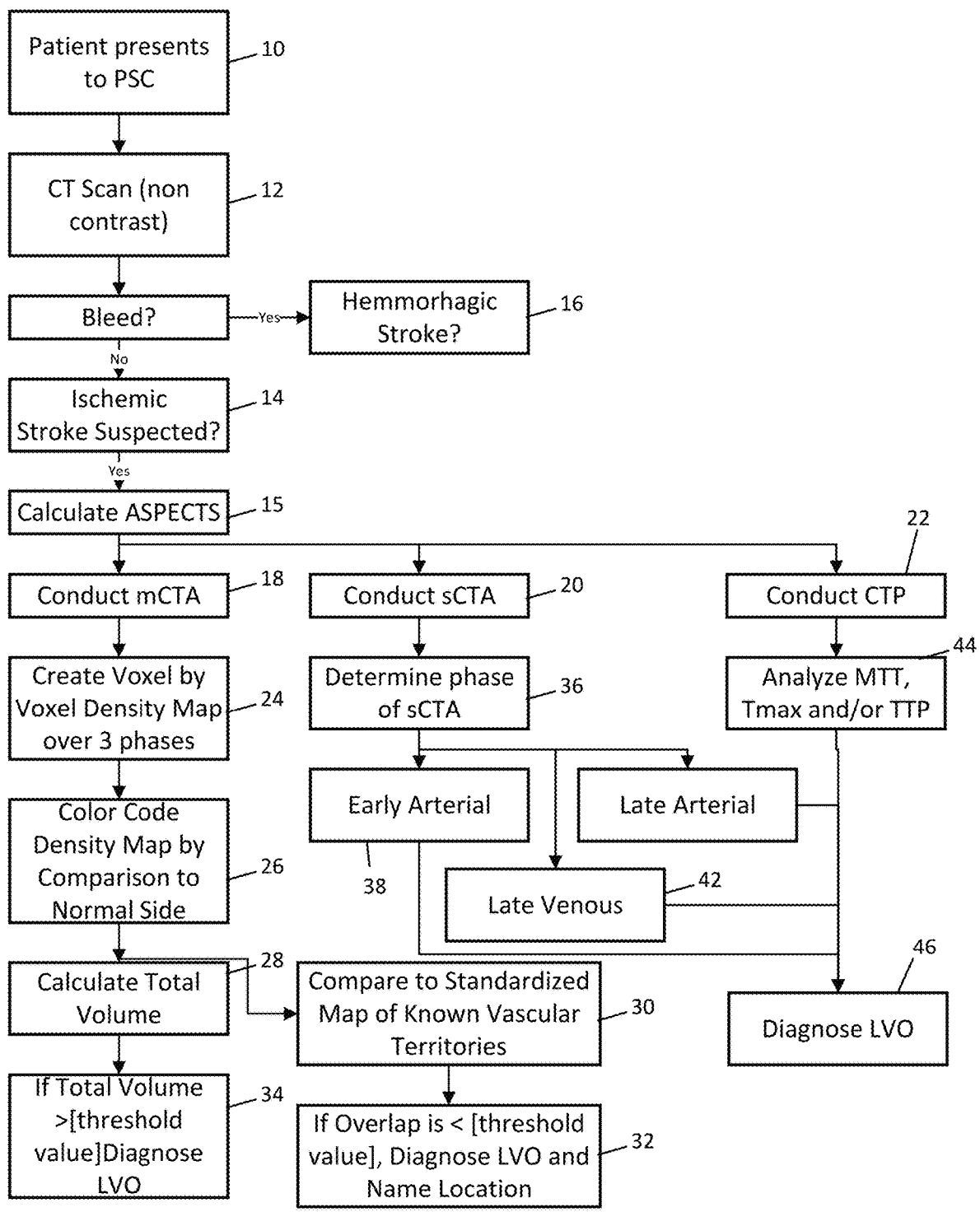
FIG. 1 is a flow chart showing diagnostic processes in accordance with the invention.

In accordance with the invention and as shown in FIG. 1, the steps include a) conducting a CT head followed by either a CTA or multiphase CTA and/or CTP at a PSC; and b) processing the images using automated software to either quantify the ASPECTS score and/or the presence/absence of LVO.

From steps a) and b), the processed information can be used to make patient transfer/movement decisions.

The invention is described with reference to typical stroke diagnosis and CT imaging procedures.

Process

After a physician has presented to a PSC 10 and conducted a non-contrast CT scan 12, they may decide that it is likely that the patient has suffered an ischemic stroke 14 or a hemorrhagic stroke 16. If an ischemic stroke is suspected, a decision may be made to conduct a CT angiogram (including an sCTA 20, or mCTA 18 and/or CTP 22) in which one or more set of images is obtained using a contrast agent.

Figure 1A:
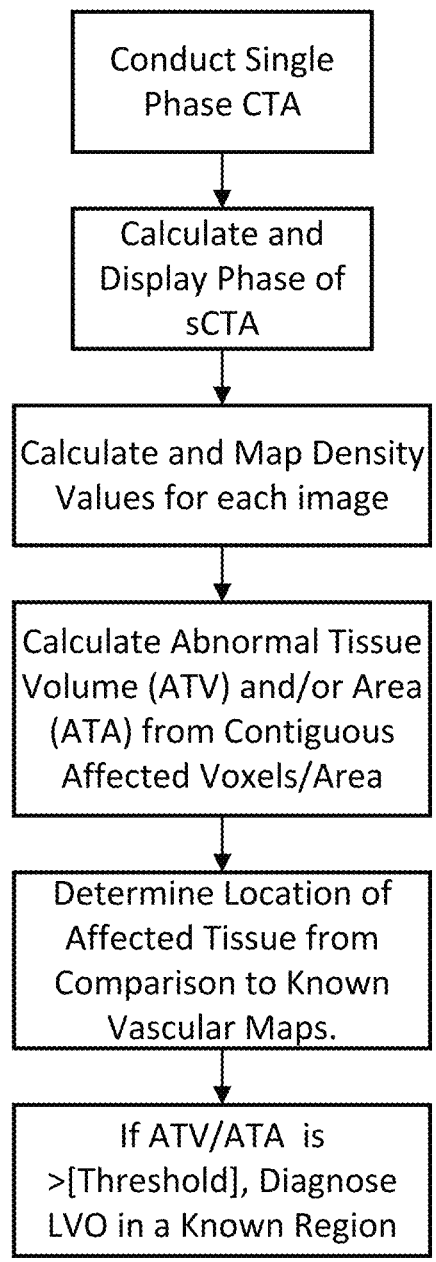
FIG. 1A is a flow chart showing a diagnostic protocol from a single phase CTA (sCTA) where the phase of the sCTA is determined in accordance with one embodiment of the invention.

For the purposes of initial description the CT angiogram is performed using the multiphase technique (mCTA 18) as described in detail in U.S. Pat. No. 9,324,143 and incorporated herein by reference. However, other approaches, while not optimal could be performed on a single phase sCTA 20 as described below (see FIGS. 1A and 1B) or data from a CT perfusion (CTP 22) study described below. Prior to conducting CT angiogram studies, ASPECTS may be calculated from manual or automatic procedures 15.

During a standard CT angiogram, a bolus of contrast agent (dye) is injected into the patient typically into the forearm. A typical bolus may be injected at a rate of 5 cc/second for 15 seconds. As it is injected, the dye travels to the right side of the heart, through the lungs and into the left side of the heart.

The CT technologist monitors the circulation time of the dye by repeated scanning typically at the level of the aortic arch and when the dye emerges from the left ventricle and it reaches the aortic arch, the CTA machine is triggered. The CTA is conducted in the upward direction (that is successive images are taken from the lower cerebral regions to the top of the head) and will typically take about 5 seconds to complete with a newer CT machine. Hence the images are generally timed to chase the peak dye levels as the dye travels through the arterial vessels of the brain. Hence, on the normal side of the brain (i.e. the side that has no occlusion or suspected occlusion) the dye will be fully saturating the brain arteries as the images are being collected. Thus, these images will show high density, that is a lighter color on the CT images.

Subsequently, additional phases of CT images are obtained (practically 1-5 additional phases) after waiting for a short period of time (as described in detail in U.S. Pat. No. 9,324,143).

The dye also travels to the ipsilateral (affected side) and if an occlusion is present, generally, the contrast takes time to reach the affected tissue as it has to travel a longer path through collaterals. In addition, the cerebral blood flow through the affected tissue is lower (which is why the patient is having stroke symptoms) and hence the transit time of contrast is slower. Thus the peak opacification of the vessels in the affected territory is slower and the clearing out of contrast is slower.

Corresponding to the opacification of the vessels, there is a change in the density of the brain tissue as well as the contrast reaches the capillaries.

Thus every voxel of brain tissue (as defined by the CT machine software) has a transient rise in density (as measured in Hounsfield units (HU) on the CT scan). This change of density is different between the affected and unaffected tissue.

As a result, a comparison can be made between contrast density levels on both sides. If both sides show substantially no difference in densities, there may not be any occlusion.

In a first embodiment, the invention calculates and/or displays any increase and decrease of density over time using data from the different phases of the mCTA between each voxel. This analysis may be initially conducted at a 2D level for each image which can then be interpolated between successive images to define density curves for a particular volume in 3D space and form the basis of a density map 24.

In other words, all the voxels having a significant difference in the rise and fall of density (HU) compared to the normal side are marked out.

The parameters for significant difference can also be based on parameters such as timing of peak opacification, rate of reduction of density, height of peak opacification and others. In general, it is expected that the affected side (the side with an occlusion) will have delay to peak opacification and a slower reduction of density (contrast hold up).

In various embodiments, the exact quantification of how much different is significant will be set based on validation of the methodology using existent datasets. For example, data from existing datasets may be analyzed to provide statistical significance to observations in a current patient. Other factors, such as rate of contrast injection and the total volume of contrast may enable additional information, and hence, in various embodiments, may lead to standardization of input parameters.

All voxels that have a significant difference based on various of the above mentioned parameters will be labeled as being part of the affected ischemic tissue.

Importantly therefore, if one or more additional sets of images are obtained, a clearer picture of the collateral circulation can be obtained.

When a second (P2) and third (P3) set of CT images are obtained, ideally they are timed to generally correspond to particular phases of contrast moving through the brain. Generally, the first set (P1) of images is timed to coincide with peak dye flow through the arterial side of the brain (i.e. the normal side), the second set timed to coincide with peak dye flow to the venous side of the brain (i.e. the normal side) and peak flow through affected tissue and the third set to coincide with clearance of dye through the normal side but towards the tail end of dye moving through affected tissue.

More specifically, from the different phases of images, the mean transit time (MTT) of contrast through the affected regions can be approximated. That is, as the MTT is increased on the affected side as the contrast takes longer to move past or around the blockage, flow rates are lower and thus will take longer to clear. Also, a smaller volume of dye may pass through two comparable areas on the ipsilateral and contralateral sides.

Figure 2:
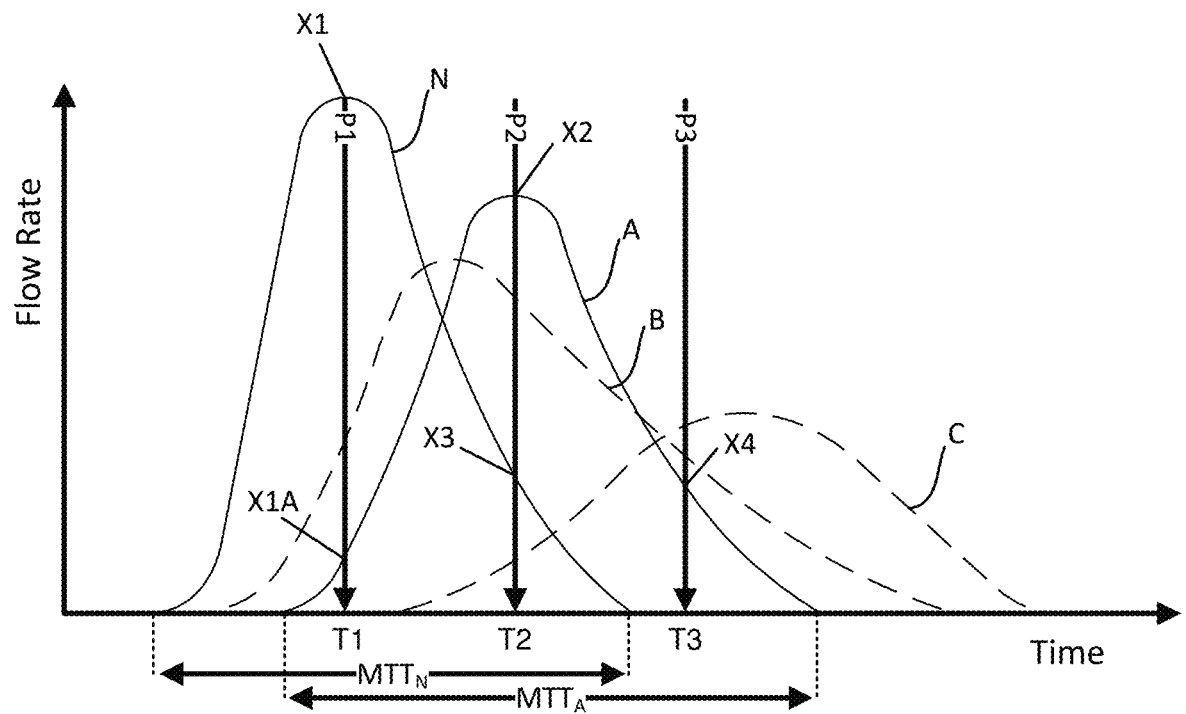
FIG. 2 is a schematic diagram of representative flow rates of contrast agent through an arterial region of the brain having affected and normal tissue.

FIG. 2 shows representative flow rates of dye passing through a corresponding volume of tissue on both the right and left side of the brain. Curve N shows the flow of dye through the normal side and can be seen to rapidly rise as the dye enters the region, stay relatively high for a period of time and then rapidly drop off as the bolus of dye ends.

Curve A shows a representative flow rate of dye through an affected volume of tissue. In this case, an obstruction is present which slows down the passage of dye into the region and/or enters the region via collateral circulation. Curve A shows that the flow rate of dye is delayed, reaches a lower peak flow and then clears. Curve B shows a situation where flow into affected tissue is delayed but takes longer to clear (referred to as "Washout") and curve C shows a situation where there is a long delay, low maximum flow rate and slow clear. In addition, the MTT of the affected side (MTTA) will be longer as compared to the MTT of the normal side (MTTN) as shown representatively for curve B. FIG. 2 also shows the potential timing of three phases of images P1, P2 and P3.

P1 which is taken substantially at peak dye flow rate through the arterial system would show strong presence of contrast throughout the arterial system. Thus, a peak concentration of dye X1 could be measured. However, the images would also show an affected region where less dye was getting through (X1A) at that moment. Hence, an affected region would be identified.

P2, which is taken substantially during peak dye flow through the venous system would show decreasing dye in the arterial normal side X3 but in this case also shows increasing dye in the affected volume X2. Thus, the data point X2 provides a first quantification of the flow rate through the affected tissue. This can then be compared to what would be expected from X1.

P3, which is taken substantially after dye has cleared the venous system, may show dye clearing out of the affected tissue. Hence a further data point X4 is obtained which can be compared to X2 as both a time and flow rate change from X2. Thus, from the measured density values and knowledge of the time of each phase, namely T1, T2 and T3, approximations of the flow characteristics can be made through the normal and affected volumes of tissue.

The foregoing is a description of flow through one volume of tissue within the brain. Analysis of the complete set of images for multiple zones allows the creation of color coded maps 26 showing the health of circulation through different zones which can be assessed quantitatively based on the location of the affected tissue to determine if an LVO is present or not.

For example, if the affected size is a sizeable portion of the MCA (middle cerebral artery), for example >50%, then an LVO must be present. In addition, the data could also show that multiple territories could be involved.

Figure 3:
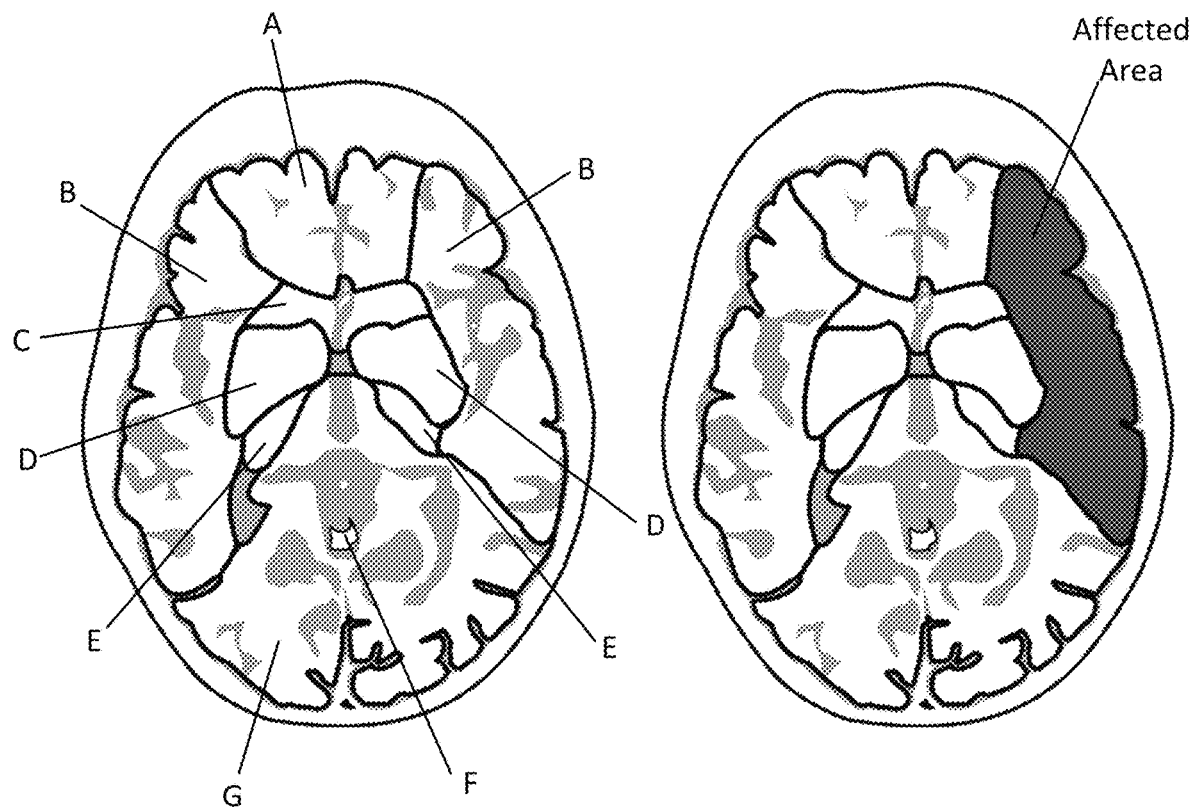
FIG. 3 is a schematic diagram showing a map of different cerebral vascular territories.

The determination of LVO can generally be done in one of two ways where known vascular regions are overlaid on a patient's images to objectively identify where the affected tissue is and, hence, the location of a potential occlusion:

A. Matching the affected area namely an area with altered blood flow that is based on predetermined factors such as time to peak, mean transit time, time for clearing of contrast. Each voxel can be color coded to create a map of showing all the 'abnormal' region (based on one or more of the above mentioned factors). This region of abnormality on the color map would displayed against a known atlas of vascular anatomy of the brain as shown in FIG. 3 where the various vascular regions of the brain are overlaid the patient's images thus showing boundaries between each vascular region and the amount of affected tissue that may lie within that known vascular region. As shown in FIG. 3 an area supplied by the middle cerebral artery is displayed as being affected. In this particular example, a considerable part of the affected territory shows an altered blood flow by comparison to the known vascular territories 30. From this map, if the difference is greater than a threshold value 32 the inference can be made that an LVO to the middle cerebral artery is present.

B. When a large number of contiguous voxels show an altered flow volume 28 and the combined volume of the affected voxels is greater than a defined threshold e.g. 50-70 ml, this can lead to the conclusion that an LVO is present 34.

Once the above calculations have been made, the PSC can be advised on the likely presence or absence of an LVO which can then used to support a decision to move the patient to a CSC.

It is noted that the definition of LVO may change with improvements in technique and technology. At the current moment, according to the AHA guidelines, patients with an occlusion to the M1 segment (the main horizontal stem) of the middle cerebral artery (MCA) should be treated with EVT. In this case substantively the entire territory supplied by the MCA would show altered flow.

It is also noted that depending on the location of the occlusion (proximal vs. distal) there may be sparing of the basal ganglia and anterior temporal region. However, this would not result in any substantive change in decision making.

Figure 3A:
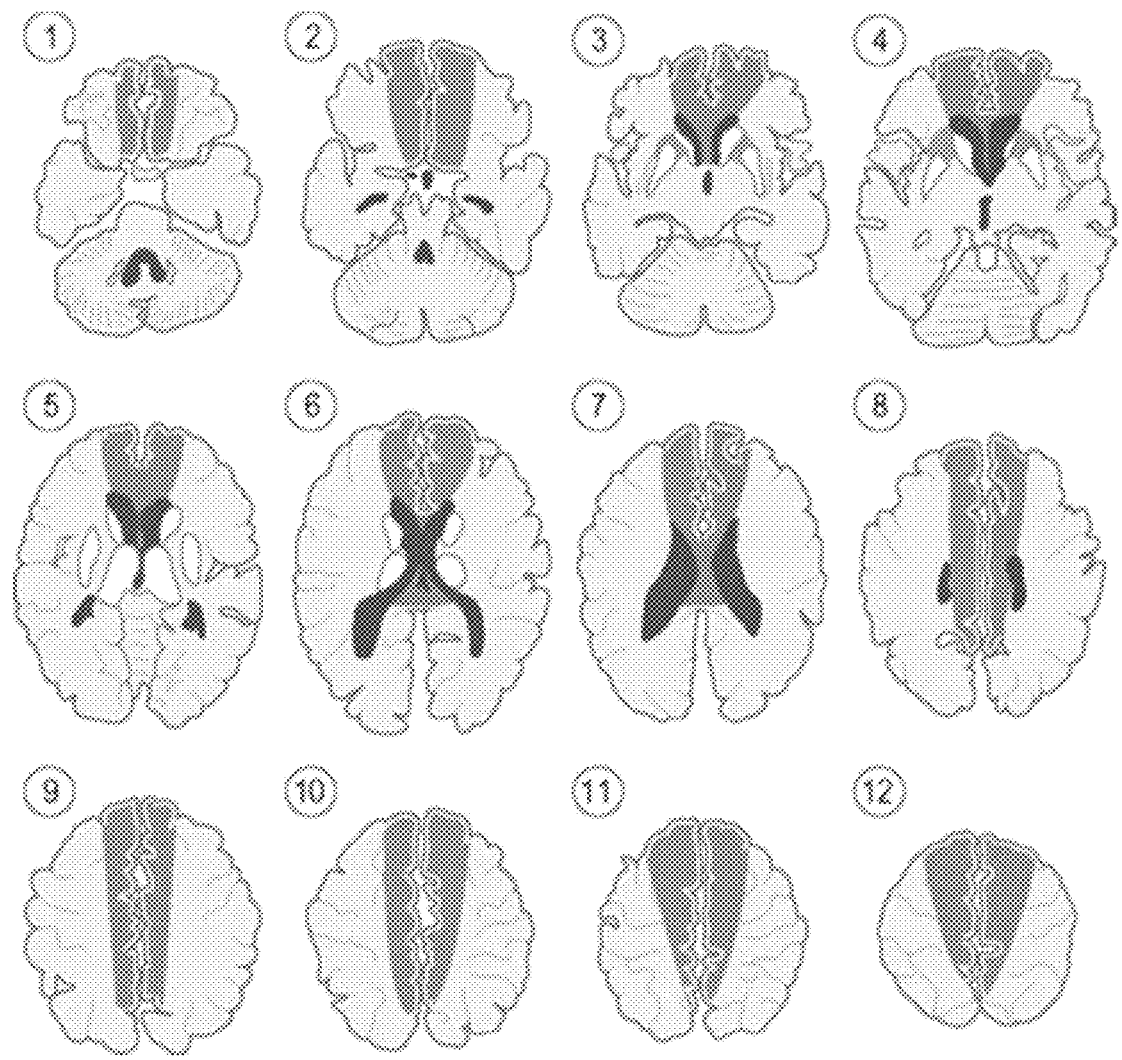
FIG. 3A is a schematic diagram showing a map of different cerebral vascular territories supplied by the M1 artery.

However, it is likely that in the near future other branches such as the M2 division (the next order division) of the MCA would also be treated by EVT. Thus, the system would be adapted to diagnosis of M2 MCA occlusion (as described above based on a contiguous involvement of voxels that add up to represent an M2 territory. For example, FIG. 3A shows an M2 territory map which could be used as the basis of comparison to quantify the amount of tissue affected by an M2 occlusion.

Figure 3B:
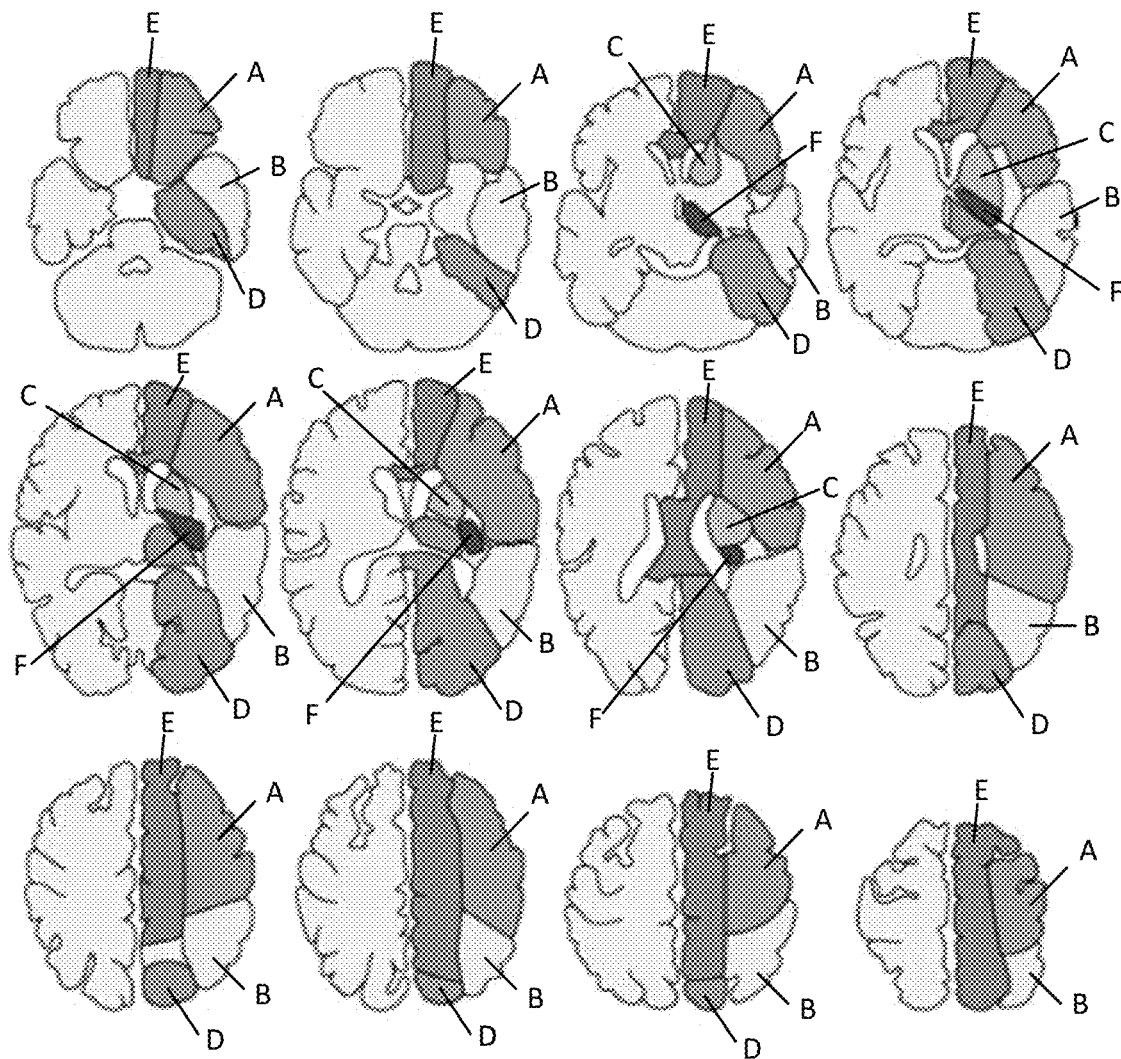
FIG. 3B is a schematic diagram showing a map of different cerebral vascular territories supplied by the ACA artery.

Similarly, as techniques progress to allow EVT for proximal anterior cerebral artery (ACA) occlusion, the same methodology would be applied to detect present of proximal ACA occlusion. For example, FIG. 3B shows an ACA territory map (Region "E" in FIG. 3B) which could be used as the basis of comparison to quantify the amount of tissue affected by an ACA occlusion.

The foregoing can be affected by various limitation including patient motion, core brain (ie. dead brain), old infarcts and/or chronic narrowing of the neck vessels that can affect MTT on both the normal and affected sides. However, these conditions are generally quite rare and usually readily seen on the non-contrast CT scan.

As noted above, conducting a single-phase CTA 20 can provide useful information but an understanding of potential pitfalls should also be understood. Depending on whether the phase of the images is determined (FIG. 1A) or not (FIG. 1B), the system in both cases can be used to provide useful information to the PSC physician. For example, if the CTA is conducted too early 38 relative to the movement of dye on the normal side, lower density values would be observed. However, these values can still be mapped and may provide a reasonable indication of flow and density and hence, be used to assist in decision making. Similarly, if the CTA is conducted too late 40, the affected side may have higher density than the normal side and cause confusion. In this case, if the physician has knowledge of which side is the affected side, and has knowledge that the phase is likely venous, these images may provide an understanding of affected tissue location and size.

If the two sides match 42, that is because of the timing of the CTA (ie. falling on the normal side and that equals the affected side density at the timing of the CTA), this could represent a number of situations that may be difficult to interpret without additional data. Equal density measurements could mean there is no issue, but could also mean an affected zone with excellent collaterals. Generally, if this situation occurs, the system may provide a warning to the PSC physician that this situation may be occurring.

Thus, under protocols when only a single phase of images is being collected, verification of the timing of the single phase of images should preferably be determined 36, to provide the best data for an accurate diagnosis. In one embodiment, monitoring the signal in Hounsfield units (HU) in different locations can provide information to ensure an understanding of when the images were taken. For example, measuring the HU signal of the basilar artery (BA) and superior sagittal sinus (SSS) could determine if the images were early or late. Generally, if the signal in the BA is more than SSS it would indicate that the affected side density may be low whereas if the SSS signal is higher than the BA signal this may indicate a late arterial/early venous.

Furthermore, another method of assessing the normal vs. abnormal side on single phase CTA is to look at arterial density vs. venous density on the normal vs. abnormal side. That is, the side that is abnormal is likely to have more venous density than arterial density although the overall density may be the same between both sides. As such, this method can be used to identify abnormal side on single phase CTA and when the two sides are then compared for arterial density differences, then LVO can be identified.

Thus, broadly speaking if the single phase CTA is early arterial, the physician would be expecting the affected side to be of lower density. Thus all voxels with a density lower by a predetermined amount compared to the opposite side would be taken to be affected by the occlusion.

If the single-phase CTA is late venous, the affected side would have higher signal compared to the normal side.

All the affected voxels would be summated in the same manner as described above for multiphase CTA and all contiguous voxels would be mapped together to compared to a standardized map of known brain vascular supply or the volume of all the summated voxels would be calculated. As noted above, preferably voxels are color coded based on density. All contiguous abnormal voxels are collected together in 3-dimensional space and then mapped against known vascular anatomy.

It would be expected that for the comparison to the opposite side: gray matter voxels would be compared to contralateral gray matter and white matter voxels would be compared to contralateral white matter.

In another embodiment, after the collation of the abnormal voxels in 3D space, the total volume of abnormal tissue if measured and if the total volume exceeds a pre-determined amount (e.g. 50 cc or 70 cc), it suggests the presence of an LVO.

Figure 1B:
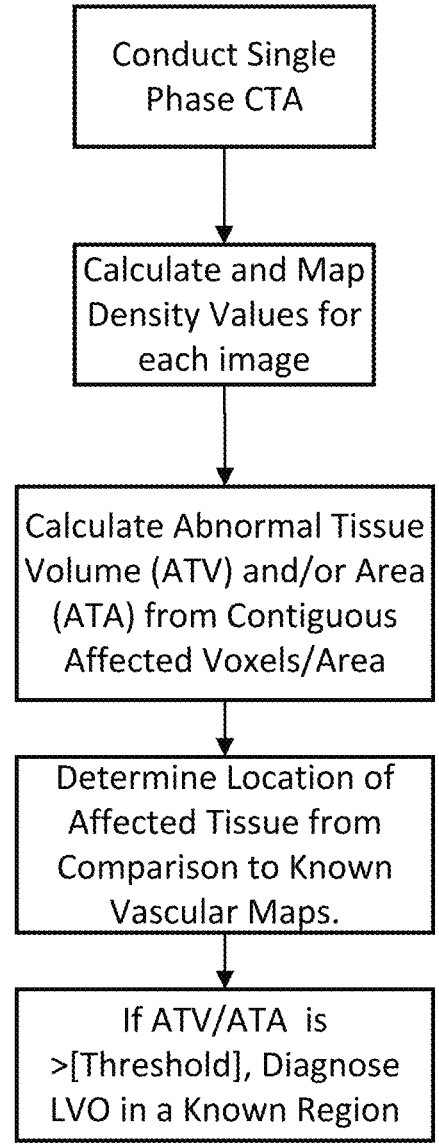
FIG. 1B is a flow chart showing a diagnostic protocol from a single phase CTA (sCTA) where the phase of the sCTA is not determined in accordance with one embodiment of the invention.

In another embodiment, using data from a single phase CTA, a density map is made as described above. The phase of the CTA is not determined (FIG. 1B). However once the map is made, the total cross-sectional area on the CT images that is abnormal is determined. It is expected that based on the site of occlusion in a patient with LVO, the cross sectional area of the affected tissue be around 40% or less (at the level of the basal ganglia and at the level corresponding to the top of the lateral ventricles). This is because it is very unusual for the PCA territory to get affected in a patient with anterior circulation LVO and usually the ACA territory is also not affected (unless there is a T occlusion (involvement of intracranial ICA, M1 and A1 with absent anterior communicating artery). The region affected would be much smaller if an M2 segment is affected only. The side with the smaller affected territory is assumed to be abnormal and matched to known vascular anatomy or the total volume calculated in 3D space as described above to determine LVO.

Other CT studies could include CT perfusion studies (CTP) 22. However, as these studies 44 are already effective in calculating MTT due to the large amounts of data collected, the same methodology could be used to detect presence of LVO 46 using automated processing and interpretation of CTP maps.

Known Territory Description and Over-Layering

While generalized maps of the vascular territories of the brain are known, there are normal variations between patients and thus, a generalized map may not be completely accurate for a particular patient. In addition, images collected from one patient are subject to variations arising from various factors including patient position and machine orientation. Hence, in one embodiment, data from numerous patients is collected and analyzed to create a library of vascular maps that may enable improved correlation between a particular patient's anatomy and previous maps which over time can be used to compensate for variations and otherwise improve the accuracy of the system and diagnosis.

Example Study—Multi-Phase CT-Angiography Maps of Parenchymal Filling Delay for Predicting Tissue Outcome in Acute Ischemic Stroke Multiphase CT-Angiography (mCTA) provides hemodynamic information of the brain's pial vasculature and has shown utility in patient selection for endovascular therapy. An assessment of blood flow in the microcirculation through quantitative mCTA maps that visualize blood flow dynamics within ischemic brain tissue was conducted to investigate if these maps help predict tissue fate on follow-up imaging.

Figure 4:
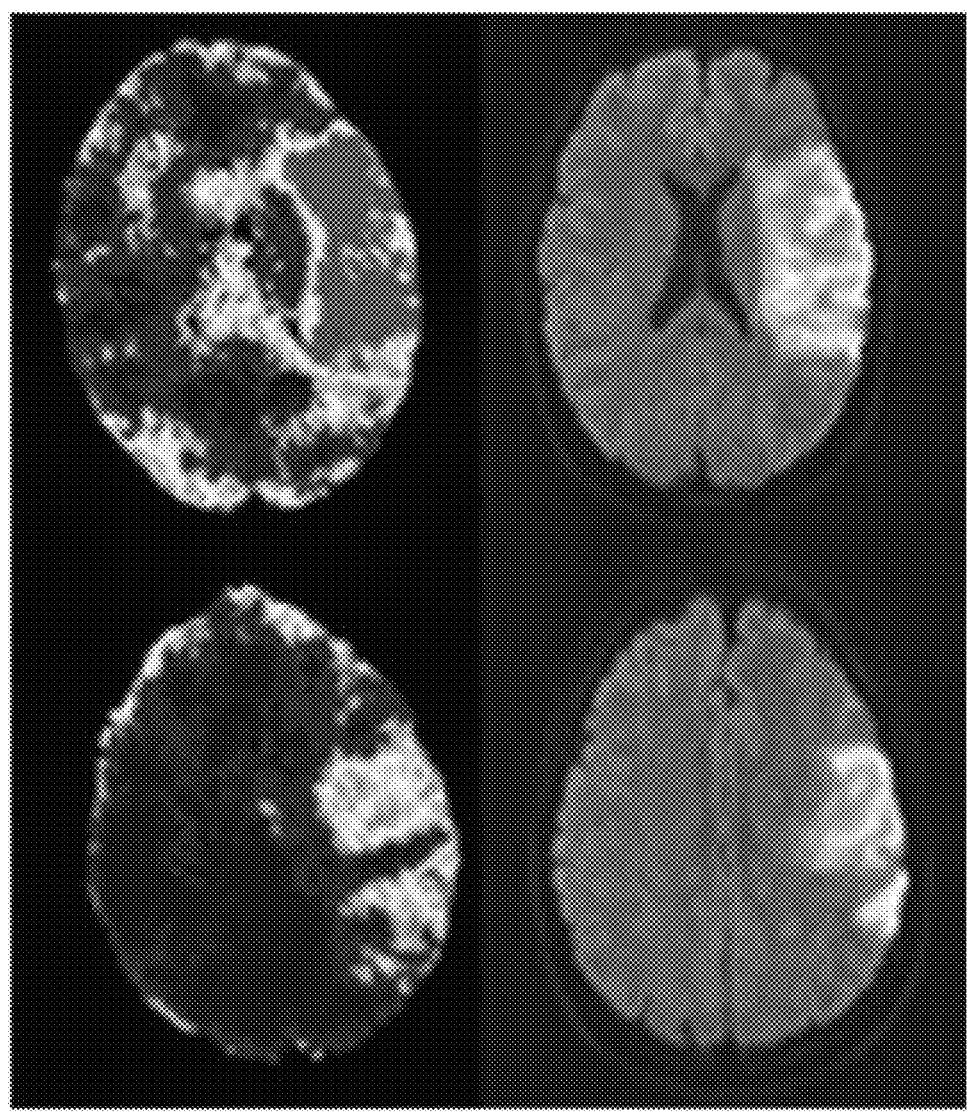
FIG. 4 is an mCTA delay map (left) of a 38 y/o female. The distribution of the delay map is the territory of an M1 MCA occlusion (matches with A of FIG. 3B). This was confirmed on the CTA that the patient did have the occlusion. The vessel was not recanalized in time. Follow-up MR-DWI (right) at 24 hours confirms that the affected area went onto to infarct.

Thirty-eight consecutive patients with follow-up MR imaging were assessed. The mCTA source images from all 3 phases of each patient were aligned to calculate the time point of maximum contrast enhancement per voxel. Large vessels were extracted prior to analysis and spatial Gaussian filtering with edge preservation was applied. The mean time point of maximum contrast enhancement of the contralateral MCA region was used as a reference value for zero delay. This reference value was subsequently subtracted from each voxel to create a quantitative map of parenchymal "delay" (FIG. 4). Follow-up infarctions were segmented on MRI (DWI preferably) and co-registered into the same coordinate space. Patients were stratified by reperfusion status (TICI 0/1 vs. TICI 2b/3). Combined patient histograms of the segmented infarctions per group were analyzed using ROC curves to determine optimal threshold to predict infarction. The AUCs were calculated to assess the discriminative value of mCTA delay maps.

The results showed that the median follow-up infarct volume of patients with TICI 0/1 (N=9) was 24.5[IQR:10.0-57.1] mL, and 11.4[IQR:2.3-42.8] mL for patients with TICI 2b/3(N=29). The optimal relative delay thresholds to predict infarction was 3.24 s and 4.13 s for the TICI 0/1 and TICI 2b/3 group, respectively. mCTA relative delay maps had AUCs of 0.84[CI:0.83-0.84] for TICI 0/1 and 0.73[CI:0.73-0.73] for the TICI 2b/3 group.

From these results, mCTA relative delay maps can be used to visualize impaired parenchymal filling and may predict follow-up infarction in acute ischemic stroke patients with and without reperfusion.

The invention claimed is:

1. A method of diagnosing a vessel occlusion in a brain, the method comprising the steps of:
   performing a multi-phase computer tomography angiogram (mCTA) on a patient to obtain at least 3 phases of mCTA images across multiple levels of the brain where the mCTA includes injecting a single bolus of contrast and where one phase of images is timed to correspond with a peak contrast flow through an unaffected side and another set of images is timed to correspond with a tail-end of contrast clearance through the unaffected side;

measuring contrast agent density across the phases of mCTA images and displaying contrast agent density on images based on a color scale for different densities;

over-layering boundaries of known vascular regions of each level and calculating an amount of affected tissue voxels in the known vascular regions above a threshold density value; and comparing the amount of affected tissue voxels within the known vascular regions to a threshold to diagnose or not occlusion in a supply artery to the known vascular region.

2. The method as in claim 1 where each phase of mCTA images includes a time value and time differences between each phase and density values are utilized to calculate any one of or a combination of a rate of rise/fall in density, time of peak opacification and mean transit time (MTT).

3. The method as in claim 1 wherein a rate and volume of contrast injection is known and correlated to contrast density measurements.

4. The method as in claim 1 further comprising the step of color coding each voxel of a phase of mCTA images according to blood flow as calculated from any one of or a combination of time to peak, mean transit time and time to clear.

5. The method as in claim 1 where variations in boundaries between known vascular regions between patients are analyzed from a pool of past data and correlated to a current patient to improve determination of a patient's vascular regions and threshold values for diagnosing vessel occlusion.

6. The method as in claim 1 wherein the step of calculating an amount of affected tissue includes the step of interpolating density values between the mCTA images at different levels.

7. The method as in claim 1 wherein a plurality of CT images are obtained using a multi-phase CTA (mCTA) protocol and the images of each phase are analyzed to calculate an area or volume of affected tissue by an analysis of all phases.

8. The method as in claim 7 wherein the multi-phase CTA (mCTA) protocol includes 3 phases and phase 1 is timed to correspond to peak arterial flow of contrast through the contralateral side, phase 2 is timed to correspond to peak venous flow of contrast through the contralateral side and phase 3 is timed to correspond to flow of contrast from the ipsilateral side.

9. A method of diagnosing a vessel occlusion in a brain, the method comprising the steps of:

performing a computer tomography angiogram (CTA) on a patient to obtain a single phase of CTA images across multiple levels of the brain where the CTA includes injecting a single bolus of contrast;

measuring contrast agent density across the CTA images and displaying contrast agent density on images based on a color scale for different densities; over-layering boundaries of known vascular regions of each level and calculating an amount of affected tissue voxels in the known vascular regions above a threshold density value; and comparing the amount of affected tissue voxels within the known vascular regions to a threshold to diagnose or not occlusion in a supply artery to the known vascular region.

10. The method as in claim 9 further comprising the step of calculating the phase of the single phase CTA images as early arterial, late arterial or venous based on a measurement of relative density of known arterial and venous structures during CTA.

11. The method as in claim 9 where variations in boundaries between vascular regions between patients are analyzed from a pool of past data and correlated to a current patient to improve determination of a patient's vascular regions and threshold values for diagnosing vessel occlussion.

12. The method as in claim 9 where if the phase of the series of CTA images is not calculated and density measurements between the ipsilateral and contralateral sides are within a middle range, displaying a warning to the physician that a mis-diagnosis is possible.

13. The method as in claim 9 further comprising determining an ischemic brain hemisphere by calculating differences in arterial vs venous density in each cerebral hemisphere independently.

* * * * *